United States Patent
Sasaki

(10) Patent No.: US 8,610,583 B2
(45) Date of Patent: Dec. 17, 2013

(54) ABNORMALITY DETECTING DEVICE FOR HEART ASSIST DEVICE, METHOD FOR DETECTING ABNORMALITY OF HEART ASSIST DEVICE, AND ABNORMALITY DETECTING PROGRAM

(75) Inventor: Shuhei Sasaki, Hyogo (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 539 days.

(21) Appl. No.: 12/988,652

(22) PCT Filed: Jul. 13, 2009

(86) PCT No.: PCT/JP2009/062655
§ 371 (c)(1),
(2), (4) Date: Oct. 20, 2010

(87) PCT Pub. No.: WO2010/050273
PCT Pub. Date: May 6, 2010

(65) Prior Publication Data
US 2011/0032107 A1    Feb. 10, 2011

(30) Foreign Application Priority Data
Oct. 31, 2008 (JP) .................. 2008-281803

(51) Int. Cl.
*G08B 1/08*     (2006.01)
*G08B 23/00*    (2006.01)
*A61N 1/00*     (2006.01)
*A61M 16/00*    (2006.01)

(52) U.S. Cl.
USPC .............. 340/573.1; 340/539.11; 340/539.12; 340/539.13; 607/59; 607/60; 128/203.13

(58) Field of Classification Search
None
See application file for complete search history.

(56) References Cited

U.S. PATENT DOCUMENTS

| 6,042,532 | A | 3/2000 | Freed et al. |
| 6,095,984 | A | 8/2000 | Amano |

(Continued)

FOREIGN PATENT DOCUMENTS

| JP | 2261465 A | 10/1990 |
| JP | 9173443 A | 7/1997 |

(Continued)

OTHER PUBLICATIONS

ISR for PCT/JP2009/062655 mailed Aug. 11, 2009.

(Continued)

*Primary Examiner* — Julie Lieu
(74) *Attorney, Agent, or Firm* — Kanesaka Berner & Partners, LLP

(57) ABSTRACT

In order to provide an abnormality detecting device for a heart assist device, a method for detecting an abnormality of a heart assist device and an abnormal state of a heart assist device detecting program which can early detect an abnormal state, the abnormality detecting device for a heart assist device according to the present invention includes a user information acquiring means for obtaining user information that indicates an operation state of the heart assist device implanted in a body of a user or a biological state of the user measured by the heart assist device and associating said user information with time to store in a history information storing means, and an abnormal state judging means for referring said history information storing means and judging whether or not an abnormal state is present based on a history of said user information.

12 Claims, 3 Drawing Sheets

(56) References Cited

U.S. PATENT DOCUMENTS

| | | | |
|---|---|---|---|
| 6,098,405 A | 8/2000 | Miyata et al. | |
| 6,132,363 A | 10/2000 | Freed et al. | |
| 6,351,675 B1* | 2/2002 | Tholen et al. | 607/59 |
| 6,442,433 B1 | 8/2002 | Linberg | |
| 6,648,823 B2* | 11/2003 | Thompson | 600/300 |
| 7,265,676 B2* | 9/2007 | Gordon et al. | 340/573.1 |
| 7,563,225 B2* | 7/2009 | Sugiura | 600/17 |
| 8,374,694 B2* | 2/2013 | Kelly et al. | 607/30 |
| 8,388,542 B2* | 3/2013 | Zhang | 600/485 |
| 2005/0203469 A1 | 9/2005 | Bobroff | |
| 2005/0283198 A1* | 12/2005 | Haubrich et al. | 607/30 |
| 2006/0247709 A1* | 11/2006 | Gottesman et al. | 607/30 |
| 2009/0281598 A1* | 11/2009 | Haubrich et al. | 607/60 |
| 2010/0152815 A1* | 6/2010 | Vandanacker | 607/60 |
| 2010/0161003 A1* | 6/2010 | Malmberg et al. | 607/60 |
| 2010/0268304 A1* | 10/2010 | Matos | 607/60 |
| 2010/0274322 A1* | 10/2010 | Drew | 607/60 |
| 2011/0015693 A1* | 1/2011 | Williamson | 607/30 |
| 2011/0160549 A1* | 6/2011 | Saroka et al. | 600/301 |
| 2011/0208268 A1* | 8/2011 | Brown | 607/60 |
| 2011/0264165 A1* | 10/2011 | Molnar et al. | 607/45 |

FOREIGN PATENT DOCUMENTS

| | | |
|---|---|---|
| JP | 2001222445 A | 8/2001 |
| JP | 2001344678 A | 12/2001 |
| JP | 2002505919 T | 2/2002 |
| JP | 2003135497 A | 5/2003 |
| JP | 2003521260 T | 7/2003 |
| JP | 2004129777 A | 4/2004 |
| JP | 2004211579 A | 7/2004 |
| JP | 2005080982 A | 3/2005 |
| JP | 3635663 B2 | 4/2005 |
| JP | 2006212443 A | 8/2006 |
| JP | 2006320735 A | 11/2006 |
| JP | 2004528278 A | 10/2007 |
| JP | 2007528278 A | 10/2007 |
| WO | 99/16481 A1 | 4/1999 |
| WO | 99/45981 A1 | 9/1999 |

OTHER PUBLICATIONS

Office Action corresponding to CN200980120002.1, dated Feb. 4, 2013.

Office Action as mailed on May 1, 2013, in corresponding Japanese Application No. 2008-281803.

* cited by examiner

Fig. 3

| TIME | USER INFORMATION ||||||
| | BIOLOGICAL INFORMATION || OPERATION INFORMATION ||||
| | BLOOD PRESSURE | BLOOD GLUCOSE LEVEL | VOLTAGE OF THE LIQUID PUMP | CURRENT OF THE LIQUID PUMP | CONSUMED POWER OF THE LIQUID PUMP | SUBSTRATE TEMPERATURE OF THE EXTERNAL CONTROLLER | REMAINING AMOUNT OF THE BATTERY |
|---|---|---|---|---|---|---|---|
| $t_1$ | ... | ... | ... | ... | ... | ... | ... |
| $t_2$ | ... | ... | ... | ... | ... | ... | ... |
| $t_3$ | ... | ... | ... | ... | ... | ... | ... |
| ... | ... | ... | ... | ... | ... | ... | ... |
| CURRENT($t_n$) | ... | ... | ... | ... | ... | ... | ... |

ABNORMALITY DETECTING DEVICE FOR HEART ASSIST DEVICE, METHOD FOR DETECTING ABNORMALITY OF HEART ASSIST DEVICE, AND ABNORMALITY DETECTING PROGRAM

RELATED APPLICATIONS

The present application is national phase of International Application Number PCT/JP2009/062655 filed Jul. 13, 2009, and claims priority from, Japanese Application Number 2008-281803 filed Oct. 31, 2008.

TECHNICAL FIELD

The present invention relates to a device for detecting abnormality of a heart assist device, a method for detecting abnormality of a heart assist device, and a program for detecting abnormality of a heart assist device.

BACKGROUND ART

In recent years, medical equipments have been highly developed. Following the development of the medical equipments, the medical equipments have been miniaturized. Heart assist devices have also been miniaturized to be implanted into a body of a user. The heart assist device is implanted into the body to be carried by a patient.

An alarm unit is indispensable to a heart assist device carried by a patient. Generally, the alarm unit is configured to acquire biological information of the patient or operation information of the unit itself. When abnormality is detected in the biological information or the operation information, the alarm unit informs an alarm to a patient through a buzzer or a lamp. When the alarm is informed, the patient contacts a doctor or the like. The doctor who has received contact heads for the patient and performs proper treatment.

In Japanese patent publication JP-2004-211579A (document 1), technique related to a medical device with an alarm unit is disclosed. In document 1, a technology is disclosed, whose purpose is to provide a function for judging whether or not a housing of a pump is filled with blood, in a liquid pump device for supplying medical liquid such as blood.

SUMMARY OF INVENTION

If the abnormality can be detected early, the abnormality can be dealt with early. As a result, a patient is less affected.

Therefore, an object of the present invention is to provide a device for detecting abnormality of a heart assist device, a method for detecting abnormality of a heart assist device, and a program for detecting abnormality of a heart assist device, which can early detect the abnormality.

The abnormality detecting device for a heart assist device according to the present invention includes: a user information acquiring means for obtaining user information that indicates an operation state of a heart assist device installed in a body of a user or a biological state measured by the heart assist device and associating time with the user information to store in a history information storing means; and an abnormal state judging means for referring to the history information storing means to judge whether or not a state is abnormal based on a history of the user information.

According to the present invention, the judgment of the abnormal state is carried out based on the history of the user information. Since the history is used, the abnormal state is promptly detected, as compared with a case where only current information is used.

Preferably, the abnormality detecting device for the heart assist device further includes a wireless communication means for wirelessly sending an alarm signal indicating the abnormal state to a contact receiver device which is located at a distant place when the abnormal state judging means judges to be the abnormal state. According to this invention, when the abnormal state is detected, that effect is automatically informed to the contact receiver device. The user does not need to establish contact by oneself, and the treatment for the abnormal state can be promptly carried out. Furthermore, even if the user is under a serious condition and cannot establish contact by oneself, the informing can be automatically executed.

Preferably, the abnormality detecting device for the heart assist device mentioned above further includes, a location information acquiring means for obtaining location information indicating a current location, and the wireless communication means sends a signal including the location information as the alarm signal.

Preferably, the user information acquiring means, the history information storing means, and the abnormal state judging means are installed in a controller device that is connected to the heart assist device by a wire line. In this case, the wireless communication means preferably includes: a first wireless communication means provided in the controller device; and a second wireless communication means provided in a mobile terminal. The first wireless communication means preferably sends the alarm signal to the contact receiver device, via the second wireless communication means.

Preferably, the abnormality detecting device for the heart assist device mentioned above further includes, an emergency treatment informing means for generating emergency treatment information indicating contents of emergency treatment and informing the emergency treatment information around the user.

The emergency treatment informing means preferably informs the emergency treatment information by an audio output means for outputting sound, and the audio output means is preferably provided in at least one of the mobile terminal and the controller device.

Preferably, the abnormal state judging means detects a type of the abnormal state when judging to be the abnormal state. The wireless communication means preferably sends a signal indicating the type of the abnormal signal as the alarm signal.

Preferably, the wireless communication means selects the contact receiver device from a plurality of candidate contact receiver devices and sends the alarm signal to the selected contact receiver device.

Preferably, the abnormal state judging means decides an alarm level of the abnormal state when the abnormal state is detected, and the contact receiver device is preferably decided based on the alarm level.

When the heart assist device includes a liquid pump that is controlled to be in a desirable rotation speed, the user information acquiring means preferably obtains information indicating a consumed power of the liquid pump as the user information. The abnormal state judging means preferably judges whether or not a blood vessel is abnormal, based on a history of the consumed power of the liquid pump.

The heart assist device system according to the present invention includes: the abnormality detecting device for the heart assist device mentioned above; and the heart assist device installed in the body of user. The abnormal state of the heart assist device is detected by the abnormality detecting device for the heart assist device.

The method for detecting an abnormal state of the heart assist device according to the present invention includes: acquiring user information that indicates an operation state of the heart assist device implanted in a body of a user and associating time with the user information to store it; and referring to a history information storing means and judging whether or not an abnormal state is present based on a history of the user information.

The abnormal state detecting program according to the present invention is a program for realizing the method mentioned above by a computer.

According to the present invention, an abnormality detecting device of a heart assist device, a method for detecting abnormality of a heart assist device, and a program for detecting abnormality of a heart assist device are provided, which can early detect an abnormal state.

BRIEF DESCRIPTION OF DRAWINGS

FIG. 3 is a conceptual diagram showing user information.

DESCRIPTION OF EMBODIMENTS

Figure 1:
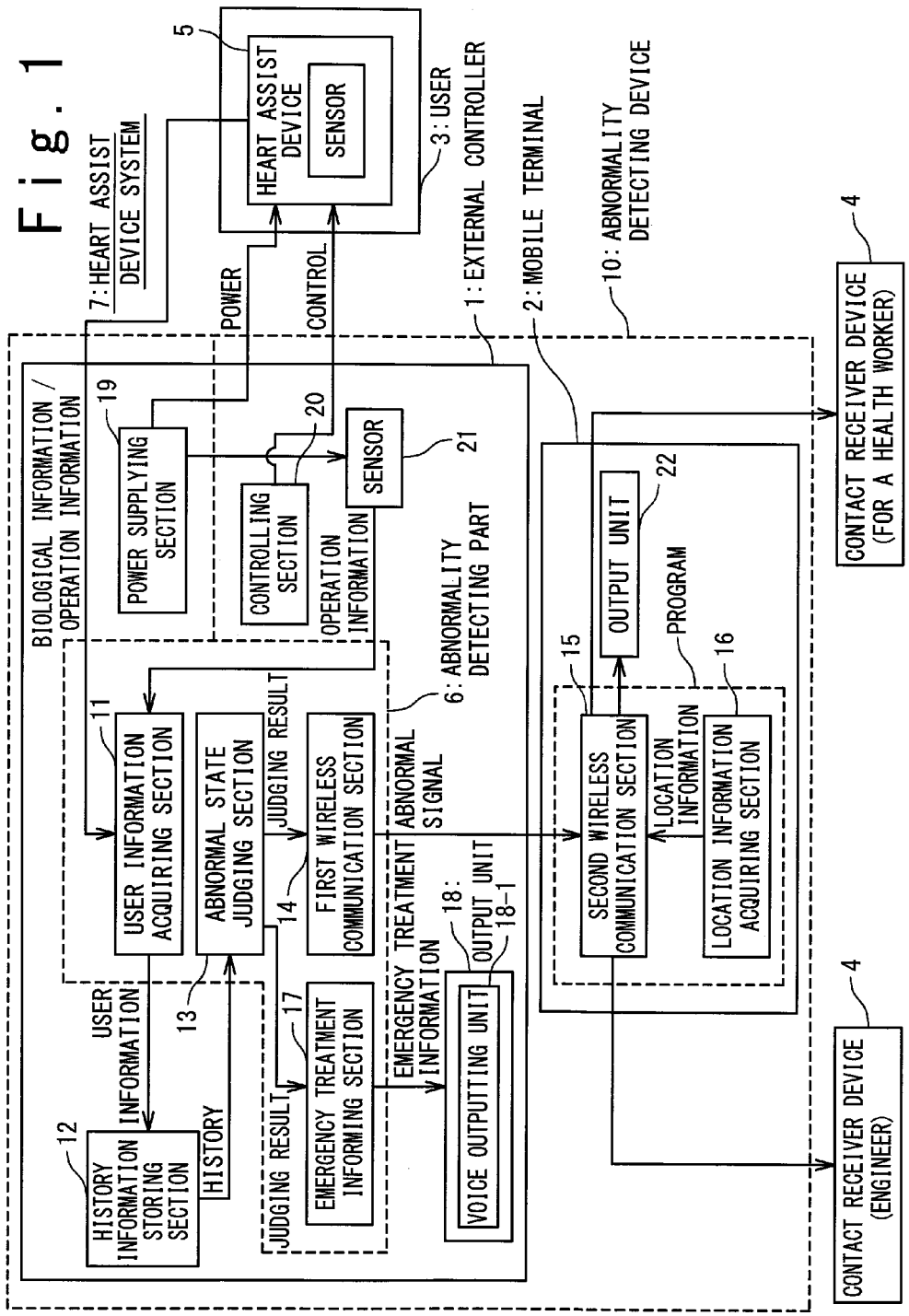
FIG. 1 is a configuration diagram schematically showing an abnormality detecting device.

An embodiment of the present invention will be described below with reference to the drawings. FIG. 1 is a schematic configuration diagram showing a heart assist device system 7 according to the present embodiment. The heart assist device system 7 has a heart assist device 5 and an abnormality detecting device 10.

The heart assist device 5 is implanted in a body of a user 3 (patient). The heart assist device 5 has a liquid pump. The liquid pump inhales and pumps the blood of the user 3. The liquid pump is operated by electric power. The heart assist device 5 notifies the abnormality detecting device 10 of an operation state of the heart assist device 5 as operation information. As the operation state, for example, a voltage value supplied to the liquid pump, a current value, power consumption, a rotation speed of the liquid pump, and a blood flow or the like can be exemplified.

Additionally, the heart assist device 5 has a sensor. The sensor measures a biological state of the user 3. The measured biological state is notified to the abnormality detecting device 10 as biological information. As the biological information, a blood pressure, a blood-glucose level, an amount of oxygen in the blood, a cardiac rate, and a body temperature or the like can be exemplified.

The abnormality detecting device 10 detects an abnormal state in the operation state of the heart assist device 5 or the biological state of the user 3. When the abnormal state is detected, the abnormality detecting device 10 sends an alarm signal to a contact receiver device 4 that is located at a distant place. The abnormality detecting device 10 has an external controller 1, and a mobile terminal 2 such as a mobile phone. The abnormality detecting device 10 is carried by the user 3.

The external controller 1 is connected to the heart assist device 5 through wired connection. The external controller 1 controls an operation of the heart assist device 5, and detects the abnormal state. The external controller 1 has a power supplying section 19, a controlling section 20, a sensor 21, an abnormality detecting part 6, a history information storing section 12, and an output unit 18. The controlling section 20 and the abnormality detecting part 6 are realized by a program stored in a recording medium such as a ROM (Read Only Memory). In particular, the abnormality detecting part 6 is realized by an abnormality detecting program.

The power supplying section 19 is exemplified by a battery, and supplies electric power to the heart assist device 5 and the external controller 1.

The controlling section 20 controls operation of the heart assist device 5.

The sensor 21 measures an operation state of the external controller 1. It can be said that the operation state of the external controller 1 also indicates an operation state of the heart assist device 5. Therefore, the sensor 21 notifies the abnormality detecting part 6 of the measurement result as the operation information. As the operation information notified by the sensor 21, for example, a voltage value of the external controller 1, a current value of the external controller 1, a temperature of a substrate provided in the external controller 1, a time for continuous run of the external controller 1, a remaining battery level in the power supplying section 19, and a condition of watchdog timer or the like can be exemplified.

The history information storing section 12 is realized by a storage medium such as a flash memory. The history information storing section 12 stores the operation information and the biological information as user information. The user information is associated with time to be stored. That is to say, the history information storing section 12 stores a history of the user information.

The output unit 18 has a voice outputting unit 18-1 (e.g. a speaker), and announces the abnormal state around the user 3 with sound.

The abnormality detecting part 6 detects the abnormal state. The abnormality detecting part 6 has a user information acquiring section 11, an abnormal state judging section 13, a first wireless communication section 14, and an emergency treatment informing section 17.

The mobile terminal 2 has a second wireless communication section 15, a location information acquiring section 16, and an output unit 22. The second wireless communication section 15 and the location information acquiring section 16 are realized by the abnormality detecting program stored in a ROM (Read Only memory) or the like. The output unit 22 includes a buzzer, a lamp, a vibration mechanism, and a display or the like.

Figure 2:
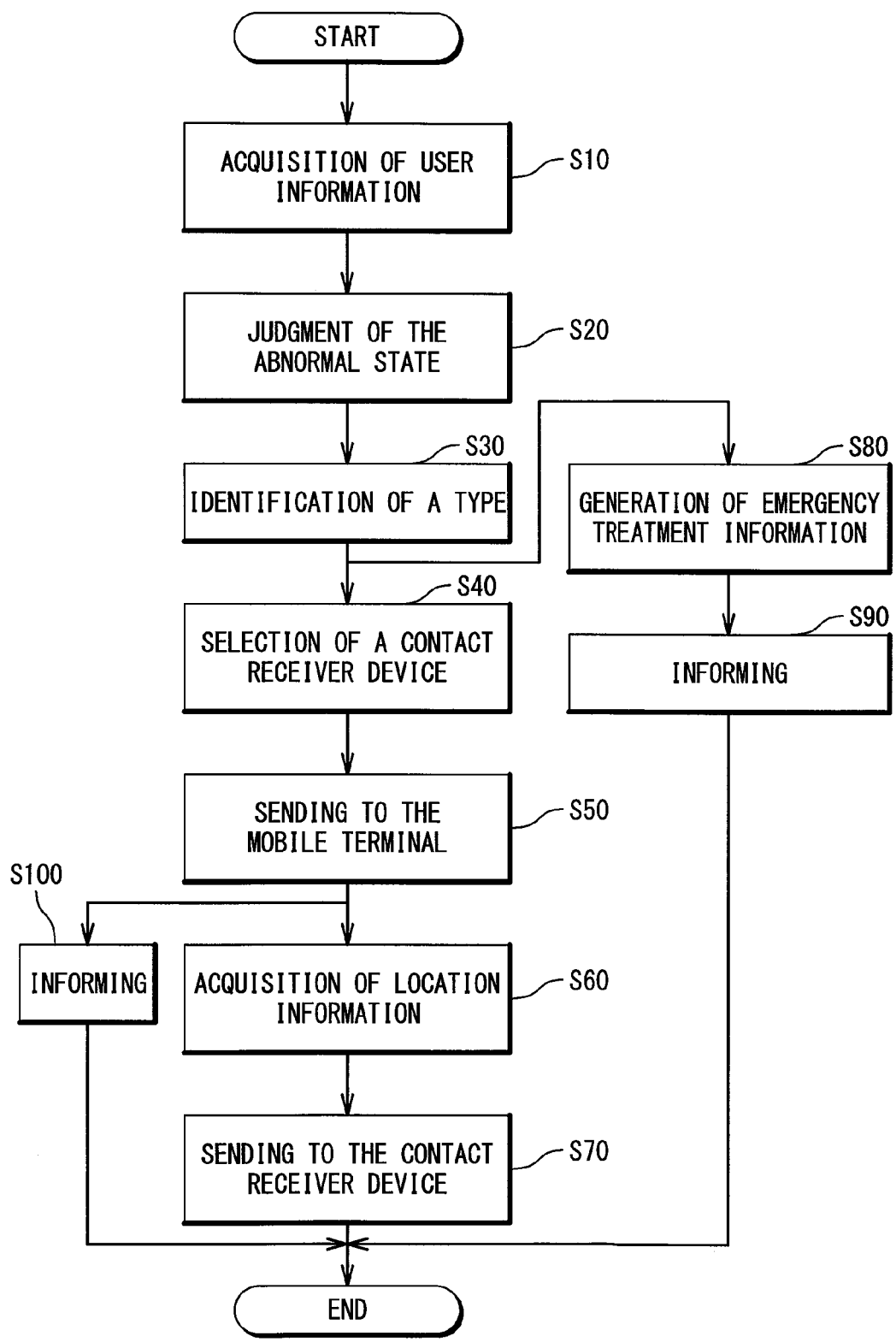
FIG. 2 is a flow chart showing an abnormality detecting method.

Next, operation method of the heart assist device system 7 will be described. FIG. 2 is a flow chart showing the operation method of the heart assist device system 7.
Step S10: Acquisition of User Information The user information acquiring section 11 acquires the operation information and the biological information at predetermined time intervals. Also, when setting of the operation state (rotation speed or the like) is changed or when the abnormal state is detected, the change and the detection are acquired by the user information acquiring section 11. The user information acquiring section 11 associates the acquired information with time, and stores it in the history information storing section 12 as user information.

In the history information storing section 12, a history of the user information up to the present is stored by the user information acquiring section 11. FIG. 3 is a conceptual diagram showing an example of data stored in the history information storing section 12. As shown in FIG. 3, user information includes biological information and operation information. In the example shown in FIG. 3, the biological information includes a blood pressure and a blood-glucose level. The operation information includes a voltage of the liquid pump, a current of the liquid pump, consumed power of the liquid pump, a substrate temperature of the external controller 1, and a remaining amount of the battery. The user information is associated with time t.

Step S20: Judgment of the Abnormal State

The abnormal state judging section 13 refers to the history information storing section 12 and judges whether or not the abnormal state is present based on the history of the user information. For example, the abnormal state judging section 13 acquires present information, information of a month ago, information of a week ago, and information of three days ago, concerning each piece of information included in the user information. Then a history pattern up to the present is obtained to be compared with abnormal reference value that is preliminarily set in a RAM (Random access memory) or the like. In a case where the present user information exceeds the abnormal reference value or a case where the user information is likely to exceed the abnormal reference value in the future, the abnormal state judging section 13 judges that the abnormal state is present. As the case where the user information is likely to exceed the abnormal reference value, a case where the user information slowly moves toward the abnormal reference value in a long period or a case where the user information is changing rapidly and is likely to exceed the abnormal reference value in the near future is considerable.

The abnormal reference value may be a constant value, but the abnormal reference value may also be a dynamic value varied based on a past operation state or the like. For example, though the details will be explained later, if the rotation speed is constant, power consumption of the liquid pump of the heart assist device 5 reflects the state of a blood flow path of the user. In such a case, an abnormal reference value concerning power consumption may be set at a maximum value of the power consumption up to the present. In this case, the abnormal reference value is set at a dynamic value.

When judging whether or not the abnormal state is present based on the history of user information, a time scale in which the user information changes is important. For example, if the power consumption increases to be a stepwise pattern in an instant, a thrombus may be occurred in a blood flow path in the upper stream of the heart assist device 5. On the other hand, when the power consumption gradually increases over several days, it is possible that a thrombus is started to be formed somewhere in the body of the user 3 and a stenosis of a flow path is caused. When the power consumption increases approximately in tens of minutes to several hours, it is possible that slight dehydration is caused and viscosity of the blood is increased. Therefore, it is possible to identify a type of the abnormal state by identifying how the user information changes.

Additionally, when judging whether or not the user information will exceed the abnormal reference value in the future, it is considered that first-order approximation of the history of user information is used. In this case, if a number of a value of the user information is larger, reliability of the first-order approximation increases. Examples about the first-order approximation will be described below.

(1) The first-order approximation is estimated based on the user information of past three minutes, and the abnormal state is judged to be present when the user information exceeds the abnormal reference value in next one minute.

(2) The first-order approximation is estimated based on the user information of the past day, and the abnormal state is judged to be present when the user information exceeds the abnormal reference value in next eight hours.

(3) The first-order approximation is estimated based on the user information of the past week, and the abnormal state is judged to be present when the user information exceeds the abnormal reference value in next three days.

As mentioned above, since judgment of the abnormal state is carried out based on the history of the user information, it can be possible to detect the abnormal state early compared with a case where only present user information is used. Additionally, since the abnormal state is judged by expecting whether or not the user information exceeds the abnormal reference value in the future, it is possible to detect the abnormal state days before the user information exceeds the abnormal reference value. Accordingly, it is possible to increase options of treatment such as medication and an operation.

Step S30: Identification of a Type

When judging that the abnormal state is present, the abnormal state judging section 13 identifies a type of the abnormal state. More in detail, for example, when the abnormal state is found in a remaining battery level among the user information, the type of the abnormal state is identified to be abnormality in a device. The abnormal state judging section 13 outputs the fact that the abnormal state is present and a type of the abnormal state as a judging result. In order to identify the type of the abnormal state, a table may be preliminarily prepared which indicates a relationship between each piece of information included in user information and a type of the abnormal state.

Step S40: Selection of a Contact Receiver Device

The judging result by the abnormal state judging section 13 is notified to the first wireless communication section 14. The first wireless communication section 14 selects an appropriate contact receiver device 4 from a plurality of candidate contact receiver deices which are preliminarily set, based on the type of the abnormal state. More than one contact receiver device 4 may be selected. For example, when the type of the abnormal state is abnormality in a device, the first wireless communication section 14 selects a device operated by a technical expert of the heart assist device system as the contact receiver device 4. For example, when the type of an abnormal state is abnormality in a biological state of the user, a device operated by a doctor or a nurse is selected as the contact receiver device 4. In order to select the contact receiver device in the above way, a relationship between the type of the abnormal state and the contact receiver devices may be set in advance.

Step S50: Sending to the Mobile Terminal

Next, the first wireless communication section 14 generates an abnormal signal and sends the abnormal signal to the mobile terminal 2 wirelessly. The abnormal signal includes the type of an abnormal state and information for identifying the selected contact receiver device 4.

Step S60: Acquisition of Location Information

In the mobile terminal 2, the second wireless communication section 15 receives the abnormal signal through an antenna (not shown). After the second wireless communication section 15 receives the abnormal signal, the location information acquiring section 16 acquires a present position as location information by using a GPS function or the like. The second wireless communication section 15 acquires location information from the location information acquiring section 16.

Step S70: Sending to the Contact Receiver Device

The second wireless communication section 15 adds location information to the abnormal signal and sends the abnormal signal to the selected contact receiver device 4 as an alarm signal. The alarm signal is sent wirelessly through the antenna (not shown).

For example, the contact receiver device 4 is realized by a computer or a mobile phone. After receiving the alarm signal, the contact receiver device 4 outputs information included in the alarm signal (e.g. the type of the abnormal state and the location information) by an output unit such as a display. An operator of the contact receiver device 4 can recognize a fact that the state of the heart assist device system 7 of the user 3 is abnormal, and a location of the user 3. Therefore, it is possible to head for the user 3 and perform proper treatment.

Step S80: Generation of Emergency Treatment Information

On the other hand, the judgment result by the abnormal state judging section 13 is also notified to the emergency treatment informing section 17 after the step S30. The emergency treatment informing section 17 generates emergency treatment information indicating the contents of emergency treatment based on the type of the abnormal state. For example, when the type of the abnormal state is biological state of the user 3, the emergency treatment informing section 17 generates a message indicating "Lie down with the head kept high", as the emergency treatment information.

Step S90: Informing (the External Controller)

The emergency treatment informing section 17 outputs the generated emergency treatment information by using the output unit 18. In the output unit 18, the voice outputting unit 18-1 informs the surroundings of the user 3 of the emergency treatment information. As a result, when a person exists around the user 3, the person can know that the user 3 is in the abnormal state. The person can treat the user 3 in accordance with the emergency treatment information. Note that the output unit 18 may have not only the voice outputting unit 18-1 but also other output units such as a buzzer, a lamp, and a display, and that emergency treatment information may be informed with using these other output units.

Step S100: Informing (the Mobile Terminal)

In the mobile terminal 2, after the second wireless communication section 15 receives the abnormal signal in the step S50, the output unit 22 informs around the user 3 that the user 3 is in the abnormal state.

As described above, according to the present embodiment, the abnormal state judging section 13 detects the abnormal state based on the history of the user information. As a result, the abnormal state can be detected early compared with a case where only present information is used.

Moreover, according to the present embodiment, the alarm signal is automatically sent to the contact receiver device 4. As an example, a case will be considered where the alarm is informed to the user 3 and the user 3 establishes contact with a doctor and so on. In this case, after the abnormal state is detected, much time is elapsed before the abnormal state is informed. In addition, there is a case where the user 3 does not notice an alarm due to surrounding environments such as noise and a situation of the user (during sleep). Furthermore, the user 3 cannot establish contact by oneself when the user 3 falls into a critical condition. On the other hand, according to the present embodiment, since the alarm signal is sent automatically, the abnormal state is notified early and certainly.

Also, according to the present embodiment, the contact receiver device 4 is selected in accordance with the type of the abnormal state, and the alarm signal is sent to the selected contact receiver device 4. For example, if the type of the abnormal state is abnormality in a device, proper treatment cannot be performed even when the abnormal state is notified to a doctor or a nurse. On the other hand, according to the present embodiment, the abnormal state can be informed to an appropriate contact receiver device.

According to the present embodiment, emergency treatment information is generated and outputted by the emergency treatment informing section 17. Consequently, the user 3 and people around the user 3 can know what emergency treatment should be performed and early perform proper treatment for the user 3.

In the present embodiment, the case was explained where the abnormality detecting device 10 included the external controller 1 and the mobile terminal 2. However, the abnormality detecting device 10 does not necessarily need to have the external controller 1 and the mobile terminal 2. For example, a function of the mobile terminal 2 described in the present embodiment may be provided in the external controller 1. Alternatively, such components as the emergency treatment informing section 17 and the voice outputting unit 18-1 included in the external controller 1 may be provided in the mobile terminal 2.

In the present embodiment, the case was explained where the type of the abnormal state was identified in the step S30, and the contact receiver device was selected based on the identification result (step S40). Here, in the step S30, the abnormal state judging section 13 may further identify degree of criticalness of the abnormal state and decide an alarm level. Then a contact receiver device may be decided based on the decided alarm level. For example, when a remaining battery level is less than two hours, operations of the steps S80, S90, and S100 and so on is performed and the alarm is informed only to the user 3. When a remaining battery level is less than an hour, a device operated by a technical expert of the heart assist device system is selected as the contact receiver device 4 in the step S40, and the alarm is informed to the technical expert. When a remaining battery level is less than 30 minutes, a device operated by a doctor is selected as the contact receiver device in the step S40, and the alarm is informed to the doctor. By deciding a contact receiver device in accordance with the alarm level in the above way, the alarm can be notified more properly.

Next, the user information will be described in detail.

In the present embodiment, the case was described where both of the biological information and the operation information are used as user information. However, it does not necessarily need to use both biological information and operation information as user information, and use of any one of biological information and operation information makes it possible to have the effect of the present embodiment.

Additionally, there is a case where the operation information reflects a biological state of the user 3. Therefore, it is possible to judge whether or not abnormality is present in the biological state of the user 3 based on the history of operation information.

As an example, a case will be explained where the rotation speed of the liquid pump of the heart assist device 5 is controlled to be a desired value by the controlling section 20. In this case, power consumption of the liquid pump reflects the state of a flow path. When a thrombus is caused in the body of the user 3, power consumption of the liquid pump becomes greater in order to maintain the rotation speed of the liquid pump at a desired value.

By using the above point, it is possible to judge whether or not abnormality is caused in a blood flow path based on a history of power consumption. That is to say, the user information acquiring section 11 acquires power consumption of the liquid pump as user information. The abnormal state judging section 13 judges whether or not abnormality is present in a flow path based on the history of power consumption. Judgment of an abnormal state concerning a thrombus is performed. When judging that an abnormal state is present, the abnormal state judging section 13 outputs "a thrombus" or "a biological state" as a type of the abnormal state. As a result, it is possible to notify the contact receiver device 4 of a type of abnormality more in detail. Additionally, it is possible to inform more proper contents as emergency treatment information.

What is claimed is:

1. An abnormality detecting device for a heart assist device, comprising:
   a user information acquiring means for obtaining user information that indicates an operation state of the heart assist device implanted in a body of a user or a biological state of the user measured by the heart assist device and associating said user information with time to store in a history information storing means; and
   an abnormal state judging means for referring to said history information storing means and judging whether or not an abnormal state is present based on a history of said user information,
   wherein said heart assist device comprises a liquid pump that is controlled by electric power such that a rotation speed is a desirable rotation speed,
   wherein said user information acquiring means acquires consumed power of said liquid pump as said user information, and
   wherein said abnormal state judging means judges whether or not the abnormal state is present in a flow path, based on a history of said consumed power of the liquid pump.

2. The abnormality detecting device for a heart assist device according to claim 1, further comprising:
   a wireless communication means for sending an alarm signal indicating the abnormal state to a contact receiver device located at a distant place, when the abnormal state judging means judges that the abnormal state is present.

3. The abnormality detecting device for a heart assist device according to claim 2, further comprising:
   a location information acquiring means for acquiring location information that indicates a current location,
   wherein said wireless communication means sends a signal including said location information as said alarm signal.

4. The abnormality detecting device for a heart assist device according to claim 2, wherein said user information acquiring means, said history information storing means, and said abnormal judging means are provided in a controller device that is connected to said heart assist device with a wire line,
   wherein said wireless communication means comprises:
   a first wireless communication means provided in said controller device; and
   a second wireless communication means provided in a mobile terminal, and
   wherein said first wireless communication means sends said alarm signal to said contact receiver device via said second wireless communication means.

5. The abnormality detecting device for a heart assist device according to claim 4, further comprising:
   an emergency treatment informing means for generating emergency treatment information that indicates contents of emergency treatment to inform around of the user, when the abnormal judging means judges that the abnormal state is present.

6. The abnormality detecting device for a heart assist device according to claim 5, wherein said emergency treatment informing means informs said emergency treatment information with an audio output device that outputs sound, and
   wherein said audio output device is provided in either one of said mobile terminal and said controller device.

7. The abnormality detecting device for a heart assist device according to claim 2, wherein said abnormal state judging means identifies a type of the abnormal state when judging that the abnormal state is present, and
   wherein said wireless communication means sends a signal indicating said type of the abnormal state as said alarm signal.

8. The abnormality detecting device for a heart assist device according to claim 7, wherein said wireless communication means selects said contact receiver device from a plurality of candidate contact receiver devices based on said type of the abnormal state to send said alarm signal to said selected contact device.

9. The abnormality detecting device for a heart assist device according to claim 2, wherein said abnormal state judging means decides an alarm level of the abnormal state when judging that the abnormal state is present, and said contact receiver device is selected based on said alarm level.

10. A heart assist device system, comprising:
    an abnormality detecting device for a heart assist device; and
    a heart assist device implanted in the body of the user,
    wherein said abnormality detecting device for a heart assist device comprises:
    a user information acquiring means for obtaining user information that indicates an operation state of the heart assist device implanted in a body of a user or a biological state of the user measured by the heart assist device and associating said user information with time to store in a history information storing means; and
    an abnormal state judging means for referring to said history information storing means and judging whether or not an abnormal state is present based on a history of said user information,
    wherein said heart assist device comprises a liquid pump that is controlled by electric power such that a rotation speed is a desirable rotation speed,
    wherein said user information acquiring means acquires consumed power of said liquid pump as said user information, and
    wherein said abnormal state judging means judges whether or not the abnormal state is present in a flow path, based on a history of said consumed power of the liquid pump.

11. A method for detecting an abnormality of a heart assist device, comprising:
    acquiring, utilizing an information acquiring system, operation information that indicates an operation state of a heart assist device implanted in a body of a user as user information, and associating said user information with time to store in a history information storage system; and
    referring to a history information storing section and judging whether or not the abnormal state is present, based on a history of said user information,
    wherein said heart assist device comprises a liquid pump that is controlled by electric power such that a rotation speed is a desirable rotation speed,
    wherein said user information acquiring system acquires consumed power of said liquid pump as said user information, and
    wherein the action of judging whether or not the abnormal state is present includes judging whether or not the abnormal state is present in a flow path, based on a history of said consumed power of the liquid pump.

12. A computer-readable-recording medium in which a computer-executable program code is stored to attain a method for detecting an abnormality of a heart assist device, which comprises:

acquiring, utilizing an information acquiring system, operation information that indicates an operation state of a heart assist device implanted in a body of a user as user information, and associating said user information with time to store in a history information storage system; and referring to a history information storing section and judging whether or not the abnormal state is present, based on a history of said user information, wherein said heart assist device comprises a liquid pump that is controlled by electric power such that a rotation speed is a desirable rotation speed, wherein said user information acquiring system acquires consumed power of said liquid pump as said user information, and wherein the action of judging whether or not the abnormal state is present includes judging whether or not the abnormal state is present in a flow path, based on a history of said consumed power of the liquid pump.

* * * * *